United States Patent
Een et al.

(10) Patent No.: US 8,647,319 B2
(45) Date of Patent: Feb. 11, 2014

(54) ABSORBENT ARTICLE COMPRISING ONE OR SEVERAL PATTERNS

(76) Inventors: Hans Een, Mölnlycke (SE); Marcus Lehto, Fotö (SE); Ulrika Carlson, Billdal (SE)

(*) Notice: Subject to any disclaimer, the term of this patent is extended or adjusted under 35 U.S.C. 154(b) by 633 days.

(21) Appl. No.: 12/743,046

(22) PCT Filed: Nov. 19, 2007

(86) PCT No.: PCT/SE2007/050867
§ 371 (c)(1),
(2), (4) Date: May 14, 2010

(87) PCT Pub. No.: WO2009/067055
PCT Pub. Date: May 28, 2009

(65) Prior Publication Data
US 2011/0118689 A1   May 19, 2011

(51) Int. Cl.
*A61F 13/15* (2006.01)
*A61F 13/20* (2006.01)

(52) U.S. Cl.
USPC ............ 604/385.27; 604/385.26; 604/385.24; 604/392

(58) Field of Classification Search
USPC .................. 604/385.24, 385.26, 385.27, 392; 442/329, 366
See application file for complete search history.

(56) References Cited

U.S. PATENT DOCUMENTS

| | | |
|---|---|---|
| 4,493,868 A | 1/1985 | Meitner |
| 5,209,801 A | 5/1993 | Smith |
| 6,291,039 B1 | 9/2001 | Combe et al. |
| 2004/0230171 A1 | 11/2004 | Ando et al. |
| 2005/0131374 A1 | 6/2005 | Otsubo et al. |
| 2005/0148990 A1 | 7/2005 | Shimoe et al. |
| 2005/0228353 A1 | 10/2005 | Thomas |
| 2006/0282054 A1 | 12/2006 | Shimoe et al. |
| 2007/0250023 A1* | 10/2007 | Strannemalm ............. 604/361 |

FOREIGN PATENT DOCUMENTS

| | | |
|---|---|---|
| EP | 0172037 A1 | 2/1986 |
| EP | 0510455 A1 | 10/1992 |
| EP | 0604729 A1 | 7/1994 |
| EP | 1452157 A1 | 9/2004 |
| EP | 1547558 A1 | 6/2005 |
| EP | 1550424 A1 | 7/2005 |
| WO | WO 2004/057110 A1 | 7/2004 |

OTHER PUBLICATIONS

International Search Report for PCT/SE2007/050867 completed Aug. 28, 2008.
Written Opinion for PCT/SE2007/050867 completed Aug. 28, 2008.

* cited by examiner

*Primary Examiner* — Jackie Ho
*Assistant Examiner* — Aundria Hairell
(74) *Attorney, Agent, or Firm* — Buchanan Ingersoll & Rooney PC

(57) ABSTRACT

An absorbent article such as a diaper, an incontinence pad, a sanitary towel or the like includes at least one elasticated area. The elasticated area includes a patterned area having a visible pattern.

16 Claims, 5 Drawing Sheets

ABSORBENT ARTICLE COMPRISING ONE OR SEVERAL PATTERNS

TECHNICAL FIELD

The invention relates to an absorbent article such as a diaper, an incontinence pad, a sanitary towel or similar comprising at least one elasticated area, the elasticated area comprising a first and a second layer of material together with a plurality of thread-shaped elastic elements oriented essentially in parallel and arranged between the layers of material, the elasticated area comprising discreet connecting elements arranged in rows to either side of each of the elastic elements, the connecting elements connecting the layers of material in such a way that, together with the layers of material, they form constricted passages, through which the elastic elements run, the elastic elements being mechanically anchored in the constricted passages.

The connecting areas connect the layers of material and form constricted passages together with the layers of material. The elastic elements run through the said constricted passages, the elastic elements being anchored in the said constricted passages.

BACKGROUND ART

A common distinguishing feature of absorbent articles such as diapers, sanitary towels, incontinence pads, etc., is that they comprise elastic areas applied to different parts of the article. For example, it is usual for absorbent articles of the all-in-one type or pant type to comprise elastic areas in the waist section and in those areas which form the leg openings of the article when it is being worn. The function of the elastic of the waist section is, on the one hand, to hold the article in place around the waist and, on the other hand, to adapt the article to the size of the wearer's waist. The primary function of the elastic in the leg openings of the article is to seal against leakage of urine and/or faeces.

Other areas of an absorbent article can naturally also comprise elastic areas.

Various methods of elasticating absorbent articles are previously disclosed, one of the most commonly encountered methods involving the anchoring of extended elastic threads intermittently between two flexible layers of material, such as two nonwoven layers or one nonwoven layer and one plastic layer, or alternative arrangements. Once the anchoring has been effected, the loading on the extended elastic threads is relieved, causing the layers of material to interact with the elastic threads and to contract as a result of wrinkling.

Various methods for the intermittent anchoring of elastic threads exist. An example of a commonly encountered method of anchoring involves the intermittent application of adhesive to elastic threads immediately before the threads are applied between two flexible layers of material.

Intermittent anchoring can also be achieved by coating the elastic thread with a heat-activated adhesive material, the application of local heating through the layers of material and the elastic thread producing local anchoring of the elastic thread.

Another method for the intermittent anchoring of elastic threads between two layers of material involves coating one or both layers of material with intermittently arranged adhesive areas and positioning the extended elastic thread over these areas before the two layers of material are connected to one another.

It is also customary to apply continuous, parallel beads of adhesive to one of the layers of material and then to arrange elastic threads essentially perpendicular to the beads of adhesive. The beads of adhesive anchor the elastic threads intermittently, at the same time as they connect the two layers of material to one another.

One method for achieving discreet adhesive areas involves the application of a continuous and essentially sinusoidal bead of adhesive to one of the flexible layers of material, followed by the application of extended elastic threads along the bead of adhesive, as described in Patent Application EP 0,172,037 A1.

In Patent Application EP 0,510,455, intermittent anchoring of an elastic thread is achieved by coating the thread with a spiral-shaped bead of adhesive running around the thread in the longitudinal direction of the thread, whereby intermittent anchoring of the elastic thread is obtained.

An alternative method of elastic anchoring is described in U.S. Pat. No. 6,291,039, in which elastic, thread-shaped elements are anchored intermittently between two flexible layers of material without the use of adhesive. In conjunction with their anchoring, the elastic threads have been extended so that the diameter of the threads has been reduced. In this extended state, the layers of material that have been arranged on both sides of the elastic threads have then been connected to one another by means of a large number of connecting elements.

The connecting elements have been arranged in pairs very close to one another to either side of the elastic threads, whereby two connecting elements arranged in pairs form a connecting area.

This means that, when the extension of the elastic threads is reduced so that the threads are drawn together in the longitudinal direction, the diameter of the threads increases causing the threads to become wedged securely in the constricted passages or tunnels which the respective connecting area forms together with the layers of material.

The connecting elements appropriately consist of ultrasonically welded areas, as described in U.S. Pat. No. 6,291,039.

Alternatively, the constricted passages can be formed by heat-welding the layers of material together to either side of the extended elastic threads.

Other methods of producing the connecting elements are naturally also conceivable.

The application of patterns in the form of texts, images, symbols or the like to absorbent articles such as diapers, sanitary towels, incontinence pads, etc., is also previously disclosed. Combinations comprising at least two of the pattern forms are also encountered.

The texts and the symbols are preferably of an informative nature, for example in the form of an instruction for the wearer, a warning text or product information such as a size indication, for example.

The images are preferably in the form of decorative patterns, product information or instructions for the user.

Patterns in the form of trademarks and/or corporate logotypes are also commonly encountered.

The pattern is usually arranged on one of the layers which form the outside of the product when it is being worn, for example on the front or the rear end section of the product, on the fastening tabs or on one of the side panels. It is a particularly common occurrence for the pattern to be arranged on the outside of the product either at or close to the waist area of the product.

The pattern can relate to instructions in respect of how the product must be put on the wearer, the suitable size of the product for a certain weight of the wearer, or the like.

Patterns of this kind are usually positioned together with other types of pattern, such as a distinctive product mark, purely decorative patterns, positioning indicators for fastening tabs, for example, indicators intended to show which part of the product must be positioned facing forwards on the wearer, and so on.

The products thus comprises different types of pattern, some intended to inform the wearer of how to use the product, some only intended to make the product more visually attractive, and some intended to warn against incorrect use.

One familiar and commonly encountered method of applying a pattern to an absorbent article is to make use of an appropriate printing technology, whereby colour pigments are applied by means of a printing roller or the like to a layer of material appropriately on the outward-oriented surface of the article.

EP 604 729 is an example of a patent which addresses the problem of obtaining a printed pattern which exhibits improved resistance to wear after it has been applied to a nonwoven layer.

Also encountered is the arrangement of a pattern on an absorbent article by positioning a label containing a pattern on the article. The label in this case can be glued or welded securely to the article.

An alternative method for creating a pattern on a layer of material involves embossing the pattern onto the layer of material. The method requires the layer of material, to which the pattern is to be applied, to change its structure when it is subjected to embossing.

Comparatively bulky materials or laminates containing such comparatively bulky materials are particularly suitable for embossing by a combination of pressure and temperature in a so-called thermal embossing apparatus or in an ultrasonic apparatus, as described in U.S. Pat. No. 4,493,868. Examples of particularly suitable materials are thermally bonded nonwoven materials containing at least a certain proportion of thermoplastic material. When a comparatively bulky nonwoven material is subjected to local embossing, that is to say when it is subjected locally to a combination of pressure and temperature, the fibres are bonded together to form a surface exhibiting greater density. Adjacent areas that are not subjected to any embossing, on the other hand, retain their unbonded, bulkier structure, in which case the bonded surface forms a visible pattern in relation to the unbonded background structure.

Patterns can also be created by embossing on non-bulky materials, such as a plastic film, in which case patterns on the surface of the material can be created by embossing selected areas.

Patent Application US 2005/0228353 describes a method for creating a pattern on a plastic film.

A disadvantage associated with previously disclosed articles consisting, on the one hand, of an elastic area comprising thread-shaped elastic elements and, on the other hand, of a pattern, is that a separate machine component is required to create the pattern and another machine component is required to anchor the elastic threads.

Production machines comprising extra machine components tend to be more expensive with regard to their purchase and maintenance. The reliability of a production machine also reduces as the number of process stages increases, which usually manifests itself in a greater number of and longer production interruptions, higher levels of material waste and greater variations in the articles that are produced.

Absorbent articles comprising a printed pattern, of the kind described above, also suffer from the disadvantage that extra costs for colour pigments must be added to the other material costs.

Accordingly, there exists a need for an improved absorbent article, in which the process for the anchoring of elastic threads and for the creation of patterns can be simplified.

Further, there also exists a need for an improved absorbent article, in which the creation of patterns can be achieved with the reduced use, or without any use, of colour pigments.

DISCLOSURE OF INVENTION

An absorbent article of the kind discussed by way of introduction has been achieved with the present invention, whereby an absorbent article in accordance with the invention essentially overcomes the problems outlined by way of introduction that were associated with previous absorbent articles.

An absorbent article embodied according to the invention is characterized primarily in that the elasticated area comprises a patterned area, connecting elements arranged in rows along at least two elastic elements, which run through the patterned area inside one and the same row, being arranged at varying distances relative to one another and/or exhibiting a varying extent parallel to the elastic elements, the connecting elements in this case forming a visible pattern.

According to the invention, a pattern is thus formed on an elasticated area by means of a differing appearance and/or a differing positioning or distribution of connecting elements that are arranged within a specific pattern area.

The expression "visible pattern" is used here to denote a pattern which can be distinguished by an observer with normal vision at a distance of approximately 30 cm.

The connecting elements according to one embodiment of the invention are arranged in pairs to either side of the elastic elements, each pair of connecting elements in this case forming a connecting area, the connecting areas together forming the visible pattern.

In a paired arrangement of connecting elements, the connecting elements in each pair can exhibit a mutually different form and/or different size, for example a different distribution along the elastic elements. It is also possible to design the connecting elements so that the connecting elements exhibit the same form and size.

The connecting elements can possess any appropriate form, such as circular, oval, irregular, rhombic, quadratic, rectangular, etc.

The connecting elements can have a different size, and connecting elements with a different form and/or size can be combined in order to achieve the desired pattern effect.

It may be appropriate for at least two of the elastic elements in a patterned area to exhibit connecting areas which consist of connecting elements arranged in pairs and which are arranged at varying mutual distances in the direction of extension of the respective elastic element. The aforementioned varying mutual distances differ for the aforementioned at least two elastic elements in such a way that the connecting areas form a visible pattern.

A visible pattern, which, for example, can consist of an image, a text or the like, is formed by varying the mutual distances of the connecting areas in a defined manner for a number of elastic elements that are arranged adjacent to one another.

The pattern according to the invention is created without requiring the addition of any extra material and without any extra manufacturing unit, which produces savings in material costs and investment costs for machinery. Furthermore, fewer manufacturing units means fewer machine units that can cause operational interruptions during production of the absorbent articles.

The pattern can be arranged on any elasticated part of an absorbent article where it is desirable to have a visible pattern which conveys a message or has a decorative function. For example, elastic raised barriers, leg elastic, elastic side panels, etc., can be provided with a pattern according to the invention. In the case of inner raised barriers, a pattern on the barriers can make these more prominent and can increase a wearer's impression that the article possesses a reliable leakage security system.

According to one embodiment, the pattern of the absorbent article is arranged on the waist elastic of the article.

The waist elastic is usually the single most visible elastic on an absorbent article, for which reason it is particularly attractive to place a pattern on the waist elastic. It is also attractive to place a pattern on the waist elastic, because the absorbent article then gives a more clothing-like impression.

According to another embodiment, the waist elastic comprising the pattern consists of a separate waistband.

Separate waistbands are commonly encountered in absorbent articles, in conjunction with which it is also customary for the waistbands to be prefabricated and supplied in the form of a roll for the production machine for diapers. The arrangement of patterns in accordance with the invention in conjunction with the prefabrication of the waistband is a simple and appealing operation in the production of prefabricated waistbands.

One embodiment is characterized in that the pattern is arranged on the waist elastic arranged in the rear end section of the article, and another embodiment is characterized in that the pattern is arranged on the waist elastic arranged in the front end section of the article. The pattern constitutes a size indication according to one embodiment.

The waist elastic according to the invention can be combined with other types of waist elastic. For example, the waist elastic on the front section can be of a different kind from that on the rear section. It can also be desirable to have separate elastic in the side sections of the absorbent article. Such additional waist elastic need not be in the form of the elastic threads according to the invention, but can comprise elastic film, elastic nonwoven, elastic foam or different kinds of elastic laminates.

The provision of a size indication on absorbent articles is particularly appreciated in the field of institutional care, where different care recipients wear different sizes, and where different sizes are stored at a central location in the ward.

According to one embodiment, the pattern constitutes a handling instruction. This can illustrate the most appropriate way of handling an article that is contaminated with faeces or the like, for example.

According to one embodiment, the pattern constitutes an image. Images can be provided to increase the cosmetic value of the article, and for information or the like.

One embodiment involves the pattern indicating which is the front and the rear respectively of the absorbent article.

This embodiment is particularly important for so-called pant diapers, which are otherwise easily applied back-to-front and with a reduced fit as a result.

The embodiment is also very important for absorbent articles that comprise an absorption body intended to face in a certain direction when being worn.

MODE(S) FOR CARRYING OUT THE INVENTION

Figure 1A:
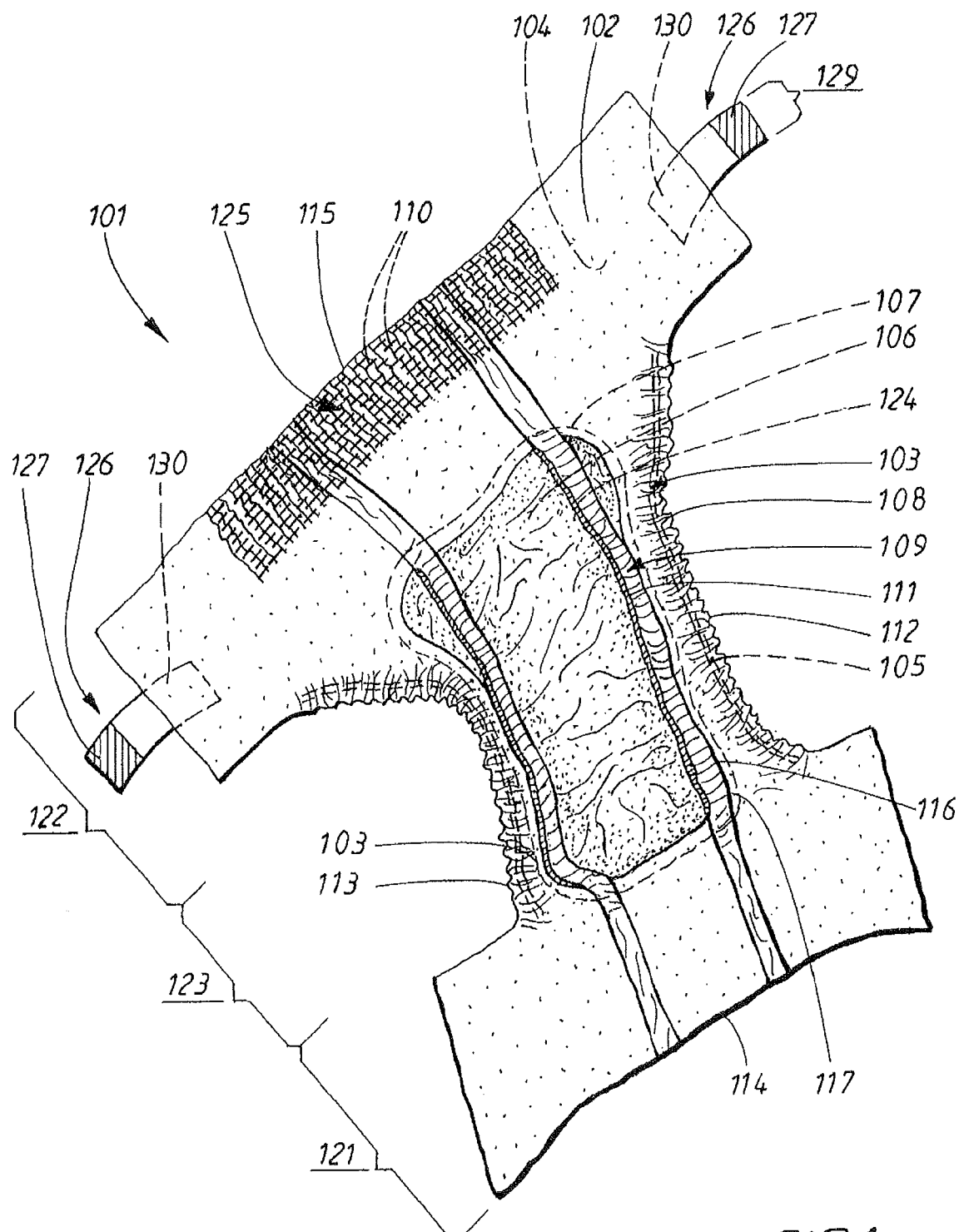
FIG. 1a depicts an open diaper according to the invention, viewed from the side that is intended to face towards the wearer when being worn.

The invention relates to an absorbent article for disposable use which exhibits an elasticated area. The elasticated area comprises a first and a second layer of material together with a plurality of thread-shaped elastic elements oriented essentially in parallel and arranged between the layers of material.

The invention also relates to an absorbent article for disposable use which exhibits a pattern, for example in the form of a text, image or symbol, which is visible to an observer from the outside of the article.

Absorbent articles in accordance with the invention are intended primarily for absorbent articles of the type all-in-one diapers, pant diapers, belt diapers or feminine hygiene products of the panty model, that is to say articles which enclose the wearer's trunk when being worn. It is naturally also possible to apply the invention to less-absorbent products such as sanitary towels, panty liners or slight incontinence pads intended to be positioned in the crotch of a wearer. However, the design and positioning of these articles in a wearer's underpants means that the arrangement according to the invention is probably less advantageous in absorbent articles of these types.

All-in-one diapers, pant diapers or belt diapers can be encountered in the form of baby diapers intended for infants who are not yet potty trained or in the form of incontinence pads intended to be worn by incontinent adults.

So-called pant diapers are characterized primarily in that they have already been folded during manufacture about an essentially transverse fold line in the crotch part of the pant diaper, and in that they have subsequently been joined together at the waist to produce a finished pant form. This type of diaper is intended to be put on a wearer precisely like a pair of underpants, that is to say passed over the wearer's legs. The join in the waist section of the pant diaper is usually capable of being separated, thereby facilitating removal of the pant diaper after use without the need to pass it all the way down over the wearer's feet when it is to be removed. This facility is particularly appreciated when the pant diaper is smeared with faeces after having been worn.

Belt diapers are characterized in that they comprise a belt oriented transversely in relation to the absorbent part of the diaper and attached to either the front or the rear transverse edge of the diaper.

Putting on a belt diaper involves securing the belt, as a first step, around the wearer's waist. The absorbent part of the diaper in this case is left hanging loosely from the belt. The absorbent part of the diaper is then passed between the wearer's legs and is attached to the belt, for which purpose the belt comprises securing surfaces intended to adhere tightly to securing devices arranged on the absorbent part of the diaper next to its free transverse edge.

So-called all-in-one diapers are characterized in that they comprise fastening tabs, by means of which the front and rear waist section of the diaper is attached when the diaper is applied around a wearer's waist.

FIG. 1a depicts essential components of a diaper 101 according to the invention.

The diaper 101 is an open diaper of the so-called all-in-one type. The diaper 101 is not joined together in the waist section at the time of sale, but is instead intended to be put on around a wearer's trunk and then to be joined together around the wearer's waist. This type of diaper 101 is in widespread use for both infants and incontinent adult wearers.

The diaper 101 essentially possesses the shape of an hourglass and exhibits longitudinal edges 112, 113, a front transverse edge 114 and a rear transverse edge 115. The diaper 101 also exhibits a front edge section 121, a rear end section 122 and a narrower crotch section 123 situated between the end sections 121, 122. The crotch section 123 is intended to be situated in the narrowest area between the wearer's thighs during use.

When the diaper 101 is being worn, the front part of the crotch section 123 and the front end section 121 essentially function as a receiving area for urine, while the rear part of the crotch section 123 and the rear end section 122 essentially function as a receiving area for faeces.

The diaper 101 comprises a liquid-permeable covering layer 102 arranged over the surface of the diaper 101 which is intended to face towards the wearer during use, a backing layer 104 arranged over the surface of the diaper which is intended to face away from the wearer during use, an absorption body 106 enclosed between the liquid-permeable covering layer 102 and the backing layer 104, and side flaps 103 arranged outside the absorption body 106.

A barrier layer 107 is arranged between the absorption body 106 and the backing layer 104.

The liquid-permeable covering layer 102 of the diaper 101 extends outside the absorption body 106 along the periphery of the entire absorption body 106. The liquid-permeable covering layer 102 can consist of any material that is suitable for the purpose. Examples of commonly encountered liquid-permeable covering materials are nonwoven textile materials, known as nonwoven materials, perforated plastic films, meshes made of plastic or textile, and liquid-permeable foam layers. Liquid-permeable covering materials consisting of continuous thin fibres, which extend primarily in the longitudinal direction or the transverse direction of the product, are also encountered. Laminates consisting of two or more of the above-mentioned possible covering materials are also commonly encountered, as are coverings consisting of different materials in different parts of the surface.

It is customary today for the liquid-permeable covering layer 102 to consist of a fully or partially elastic material in order to provide the diaper 101 with a better fit when it is being worn.

Diapers 101 comprising absorption bodies 106 which exhibit especially high strength and resistance to wear are even able to function without the need for the presence of any additional liquid-permeable covering layer on the side of the diaper 101 which faces towards the wearer when the diaper is being worn.

The barrier layer 107 also extends beyond the absorption body 106, but exhibits a smaller extension than the liquid-permeable covering layer 102, in particular in the longitudinal direction of the article.

It is common, however, for the barrier layer 107 to have the same extension as the absorption body 106. It is also possible for the barrier layer to have the same extension as the backing layer 104, or for the backing layer also to constitute a liquid barrier, in which case no separate barrier layer is required.

In certain embodiments, the barrier layer 107 can have the same extension as the backing layer 104 in the transverse direction of the diaper 101.

Normally encountered barrier layers 107 on diapers 101 are usually liquid-impermeable, although other types of backing layer are also encountered. The barrier layer 107 can consist of a number of different materials. It is most common for the barrier layer 107 to be constituted by a thin, liquid-tight plastic film, although it is also possible to use other types of liquid-tight material, such as nonwoven material, that have been made liquid-tight, for example, by coating with plastic, a liquid-tight foam layer, liquid-tight adhesive or the like. The barrier layer 107 can also consist of a liquid-tight, vapour-permeable material.

The backing layer 104 also extends outside the absorption body 106 and has the same extension as the liquid-permeable covering layer 102.

The backing layer 104 can consist of a number of different materials. It is most common for the backing layer 104 to be constituted by a nonwoven material or similar, which imparts a more clothing-like appearance to the outward-facing surface of the diaper 101 when it is being worn. The nonwoven layer is often configured in such a way that it functions as a receiving material for a hook-and-loop material of the male type. A nonwoven material of this kind is characterized in that it comprises closed fibre eyes, so-called loops, or similar elements that are capable of interacting with some kind of hook device. Just like the liquid-permeable covering layer 102, the backing layer 104 can be constituted by a fully or partially elastic material in order to provide the diaper 101 with a better fit when it is being worn.

The liquid-permeable covering layer 102 and the backing layer 104 are connected to one another outside the absorption body 106, along the periphery of the entire absorption body 106.

The liquid-permeable covering layer 102 and the backing layer 104 can be connected to one another by a plurality of different means. Examples of such connecting means include gluing, thermal fusion, ultrasonic welding or the like.

Elastic devices 105 are arranged outside the absorption body 106 in those parts of the side flaps 103 of the diaper 101 which are oriented essentially in the longitudinal direction of the diaper 101. The elastic devices 105 function as leg elastic and have the task of preventing liquid and excrement from leaking out past the longitudinal edges 112, 113 of the diaper 101 and in this way form outer liquid barriers 108 together with the surrounding layers. The elastic devices 105 consist of one or more elastic threads, which, in the extended state, have been applied between the liquid-permeable covering layer 102 and the backing layer 104, at least in the crotch section 123 of the diaper 101. The elastic devices 105 are attached to the backing layer 104 and the liquid-permeable covering layer 102 by gluing, ultrasonic welding or the like.

In alternative embodiments, the elastic devices can be arranged on the side of the side flaps 103 that is intended to face towards the wearer during use, or on the opposite side of the side flaps, in which case they are naturally only attached to the covering layer 102 and the backing layer 104 respectively.

The elastic devices in alternative embodiments can be constituted by elastic strip material, for example foam material, elastic nonwoven, elastic film, elastic laminate or the like.

The absorption body 106 can be constructed from one or a plurality of layers of cellulose fluff pulp. The cellulose fluff pulp in this case can be mixed with fibres or particles of a highly-absorbent polymer material of the kind which, in conjunction with absorption, chemically bonds large quantities of liquid to form a liquid-containing gel. The absorption body 106 can also contain highly-absorbent polymer material arranged in a layer inside the absorption body or in conjunction with the surface or surfaces of the absorption body. It is also possible for the absorption body 106 to include additional components for improving the characteristics of the absorption body 106. Examples of such components include bonding fibres, various types of liquid-dispersing layers or fibres, form-stabilizing components, reinforcing fibres or the like. The absorption body 106 can naturally also consist of other types of absorption material, such as absorbent nonwoven material, absorbent foam, textile material, peat or mixtures of various kinds of absorption material.

Special layers intended to receive quite large quantities of liquid quickly and to retain this liquid temporarily, before proceeding to release the temporarily stored liquid to other parts of the absorption body 106, can also be included in diapers of the indicated kind. Such receiving layers are normally arranged between the liquid-permeable covering layer 102 of the diaper 101 and the absorption body 106. No receiving layer is illustrated in FIG. 1.

In order further to prevent liquid or faeces from leaking out past the side edges 112, 113 of the diaper 101, the diaper 101 is provided with inner side leakage barriers 109 on the side which is intended to face towards the wearer when it is being worn. The inner side leakage barriers 109 are arranged adjacent to the longitudinal edges of the absorption body 106, and they extend essentially in the longitudinal direction of the diaper 101. The inner side leakage barriers 109 are made from separate material strips 111, which exhibit two essentially parallel longitudinal edges 116, 117. The material strip 111 is folded, the longitudinal edges 116, 117 of the material strip 111 being arranged next to one another. The edges 116, 117 of the material strip 111 are attached to the covering layer 102 and constitute the attached edge of the inner side leakage barrier. The folded edge of the material strip 111 constitutes the free edge of the inner side leakage barrier 109.

The inner side leakage barriers 109 are folded down and attached to the covering layer 102 in the front end section 121 and the rear end section 122 of the diaper 101.

The inner side leakage barriers 109 comprise elastic elements 124 attached to the inner side leakage barriers 109 in a pre-tensioned state. The elastic elements 124 are preferably arranged adjacent to the free edges of the inner side leakage barriers 109. When the pre-tensioned elastic elements 124 are released, they are caused to contract together with the free edges of the inner side leakage barriers 109, the inner side leakage barriers 109 being brought into a raised configuration away from the liquid-permeable covering layer 102, at least in the crotch area 123 of the diaper 101, where the side leakage barriers 109 are not folded down and attached to the covering layer 102.

The rear end section 122 of the diaper 101 is provided with waist elastic 125, which permits soft and flexible enfolding of the diaper around a wearer.

The waist elastic 125 in the example depicted here consists of a number of thread-shaped, essentially parallel-oriented elastic elements 110, which extend parallel to the rear transverse edge 115 of the diaper 101.

The elastic elements 110 are arranged between the two layers 102, 104 and are anchored in their extended state to the two layers 102, 104, whereby a retaining force has been obtained which tightens the diaper 101 around the waist of a wearer. When the elastic elements 110 have contracted, the two layers 102, 104 will have been wrinkled as illustrated in the figure.

In alternative embodiments, it is possible to conceive that the waist elastic consists of a prefabricated, separate waistband, in which case the elastic elements 110 have been anchored between two separate strips of material or a folded strip of material. The elasticated waistband has then been attached to the backing layer of the diaper and/or the liquid-permeable covering layer. The waistband can be manufactured in the machine that is used to produce the diapers, or it can be manufactured in advance, in which latter case it is conveniently supplied in the form of a roll to the machine which manufactures diapers.

In other alternative embodiments, it is of course conceivable for the front end section 121 of the diaper also to comprise waist elastic 125, which further increases the softness and flexibility of the diaper 101 when the diaper encircles a wearer. Such additional waist elastic can be achieved alternatively with other types of elastic materials than the threads depicted here and can comprise elastic film, elastic nonwoven, elastic foam or various kinds of elastic laminate in the same way as the leg elastic.

Arranged in conjunction with the rear end section 122 are two soft and inelastic fastening tabs 126 for holding the diaper 101 securely around a wearer. One fastening tab 126 in this case is arranged on each side section of the rear end section 122. The fastening tabs 126 connect the rear end section 122 to the front end section 121 when the diaper is being worn by the fastening tabs 126 exhibiting securing devices 127, which are capable of being affixed to a receiving part arranged on the front end section 121 of the diaper 101. The fastening tabs 126 are appropriately executed from a very soft and inelastic material, for example from a single nonwoven layer or a laminate.

The fastening tabs can be elastic in alternative embodiments.

The securing devices 127 preferably consist of male parts made of a hook-and-loop material and are attached to the fastening tabs 126, for example by means of an adhesive on the side of the fastening tabs 126 which face towards the receiving part when the diaper 101 is being worn.

The receiving part, which is not illustrated in FIG. 1, for the fastening tab 126 consists of a strip of a receiving material that is adapted to the securing device 127 of the fastening tab 126. The receiving part extends essentially parallel to the front transverse edge 114 on the side of the diaper that faces away from the wearer during use, that is to say on the side of the backing layer 104 that is oriented away from the absorption body 106. In the illustrative example described here, the material in the receiving part consists of a female part made of a hook-and-loop material and is appropriately designed so that its extension in the longitudinal direction of the diaper 101 coincides with the width 129 of the fastening tabs 126. The receiving part extends essentially over the width of the entire diaper 101 in the transverse direction of the diaper 101.

In alternative illustrative embodiments of a diaper, it is possible to conceive the arrangement of separate receiving parts for the respective securing device 127, the receiving parts being arranged in conjunction with the longitudinal edges 112, 113 of the diaper on the front transverse edge 114 of the diaper 101.

When putting the diaper 101 on an infant, the diaper 101 is positioned between the infant's legs in the area of the infant's crotch. The diaper 101 is then closed around the infant's waist by causing the fastening tabs 126 to overlap the front end section 121, so that the securing devices 127 of the fastening tabs 126 can be applied to the receiving part in order to hold the diaper securely.

The fastening tabs 126 are attached to the rear end section 122 in connecting areas 130, which are located in those areas of the rear end section 122 which lie next to the side edges 112, 113 running in the longitudinal direction. The connecting areas 130 consist of parts of the fastening tabs 126 and those parts of the rear end section 122 that are attached to one another.

In alternative embodiments, the securing devices 127 of the fastening tabs 126 can consist of a pressure-sensitive adhesive, in which case the receiving part (not illustrated in FIG. 1) consists of a material to which the selected pressure-sensitive adhesive of the securing devices 127 can be attached so that a suitable joint strength is achieved. Material combinations are usually selected so that the connection between the securing devices 127 and the receiving part can be opened and reclosed to permit inspection of the diaper 101 when it is being worn.

In other alternative embodiments, the backing layer 104 can be adapted to interact with the securing devices 127 of the fastening tabs 126, in which case no special receiving part is required.

Figure 1B:
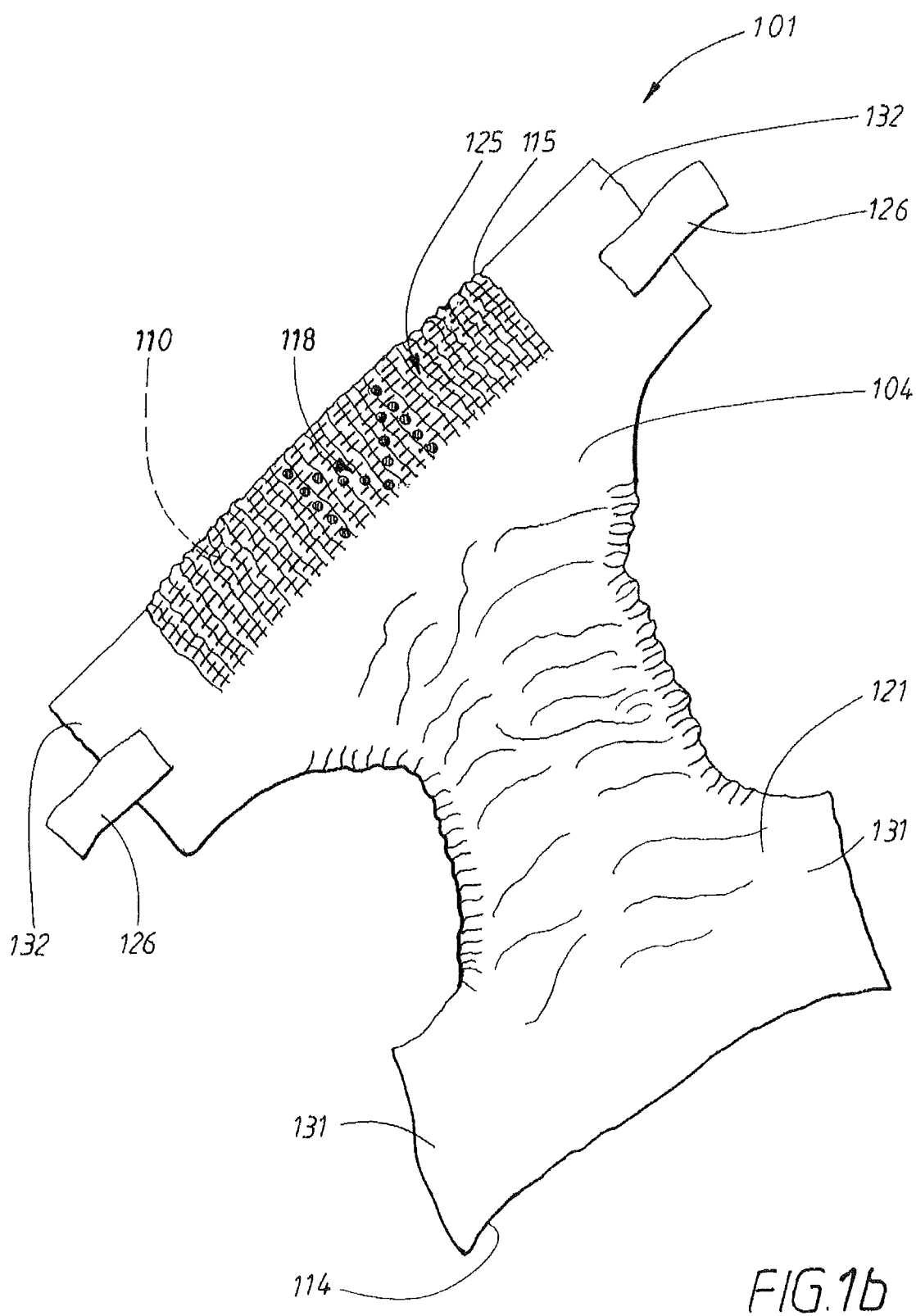
FIG. 1b depicts the diaper according to FIG. 1a, viewed from the side that is intended to face away from the wearer when being worn.

In FIG. 1b, the diaper 101 is depicted from the side that is intended to face away from the wearer when being worn.

A pattern 118, which indicates the size (M) of the diaper, is arranged in conjunction with the waist elastic 125.

Figure 2A:
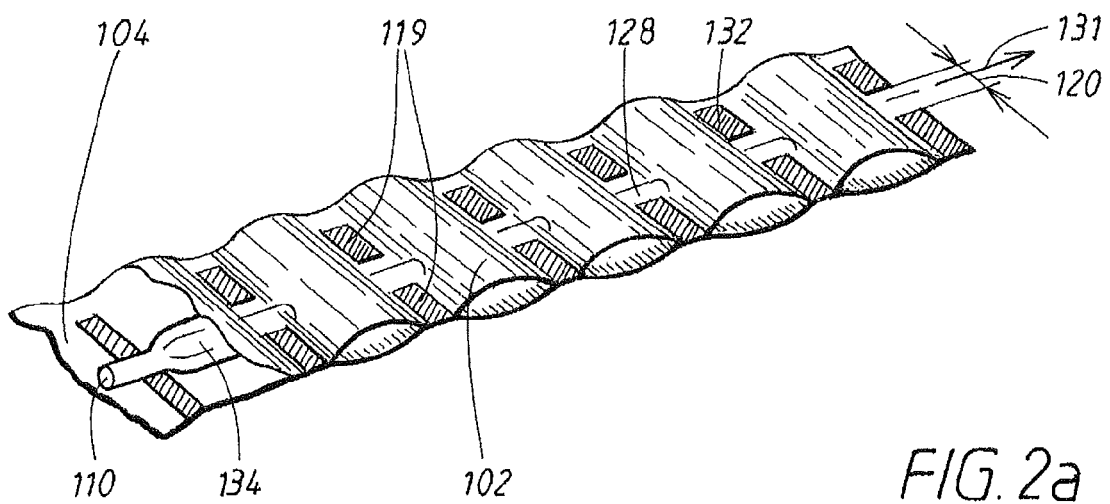
FIG. 2a depicts the principle of how an elastic element is anchored between the liquid-permeable covering layer of the diaper and the backing layer.

FIG. 2a depicts the principle of how elastic elements 110 are anchored between the liquid-permeable covering layer 102 and the backing layer 104.

The anchoring of an individual element is illustrated in the figure, although the same principle applies for anchoring all the elastic elements 110 contained in the waist elastic 125.

It is naturally also possible to conceive of anchoring other elastic areas on the diaper 101 according to the same principle.

The anchoring of the elastic elements 110 between the liquid-permeable covering layer 102 and the backing layer 104 has been achieved by first having extended the respective elastic element 110 so that its diameter has been reduced.

Connecting elements 132 have then been arranged opposite one another, to either side of the respective extended elastic elements 110, whereby two connecting elements 132 arranged essentially directly opposite one another to either side of the elastic element 110 constitute a connecting area 119.

The connecting areas 119 are arranged intermittently along the direction of extension 131 of the elastic element 110, as illustrated in FIG. 2a.

The connecting areas 119 have two functions; on the one hand, the liquid-permeable covering layer 102 and the backing layer 104 are connected to one another and, on the other hand, the elastic elements 110 are anchored between the covering layer 102 and the backing layer 104.

The connecting elements 132 that are present in a connecting area 119 are arranged in such a way as to form a constricted passage 128, the space between the two connecting elements 132 that are arranged directly opposite one another and the two layers 102, 104 constituting boundary surfaces for the passage 128.

The smallest distance 120 between two opposing connecting elements 132 constituting a connecting area 119 has been selected so that an extended elastic element 110 is actually able to run freely through the passage.

When the extension of the elastic element 110 is subsequently reduced, its diameter increases once again, in conjunction with which the elastic element 110 is no longer able to run freely inside the constricted passages 128, but is locked securely.

Between two adjacent connecting areas 119, the elastic element 110 substantially resumes its original diameter 134 once the extension of the element 110 has been released, that is to say once the elastic element 110 is free from extension. Inside the passages 128, on the other hand, the elastic element 110 is prevented from resuming its original diameter, whereby the element 110 is locked securely (anchored) in the passages 128.

The anchoring of elastic elements 110 according to the method described above is described in U.S. Pat. No. 6,291,039 (Cera France).

The connecting element 132 in FIG. 2a exhibits rectangular form, whereby one short side is arranged parallel with and adjacent to the elastic element 110.

In alternative embodiments, the connecting elements 132 can exhibit alternative forms. Circular, elliptical or triangular are examples of conceivable forms.

Figure 2B:
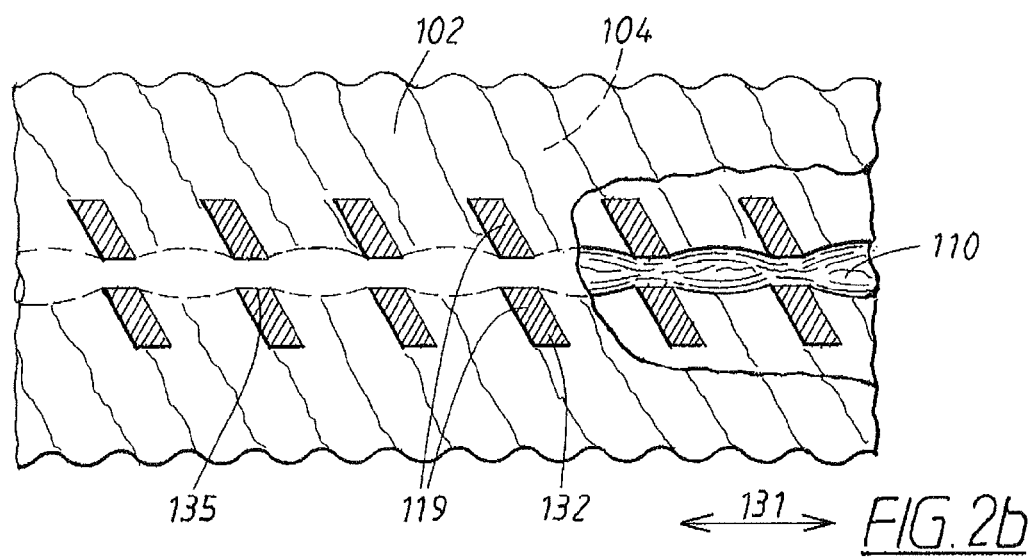
FIG. 2b depicts an elastic element anchored between the liquid-permeable covering layer of a diaper and the backing layer by means of rhombic connecting elements.

FIG. 2b depicts how an elastic element 110 is anchored between the liquid-permeable covering layer 102 and the backing layer 104, the connecting elements 132 being arranged at an angle to the direction of extension 131 of the elastic element and exhibiting rhombic form. The anchoring of an individual elastic element 110 is illustrated in the figure, which is depicted at right angles to the layers of material 102, 104, although the same principle applies to the anchoring of all the elastic elements 110 that are present in the elasticated area.

The rhombic connecting elements 132 are arranged in pairs essentially directly opposite one another to either side of the elastic element 110, two pairs of connecting elements 132 forming a connecting area 119.

The expression "essentially directly opposite one another" is used here to denote that two rhombic connecting elements 132, which together constitute a connecting area 119, are arranged with the sides 135 that are oriented towards the elastic element 110 essentially directly opposite one another.

Figure 2C:
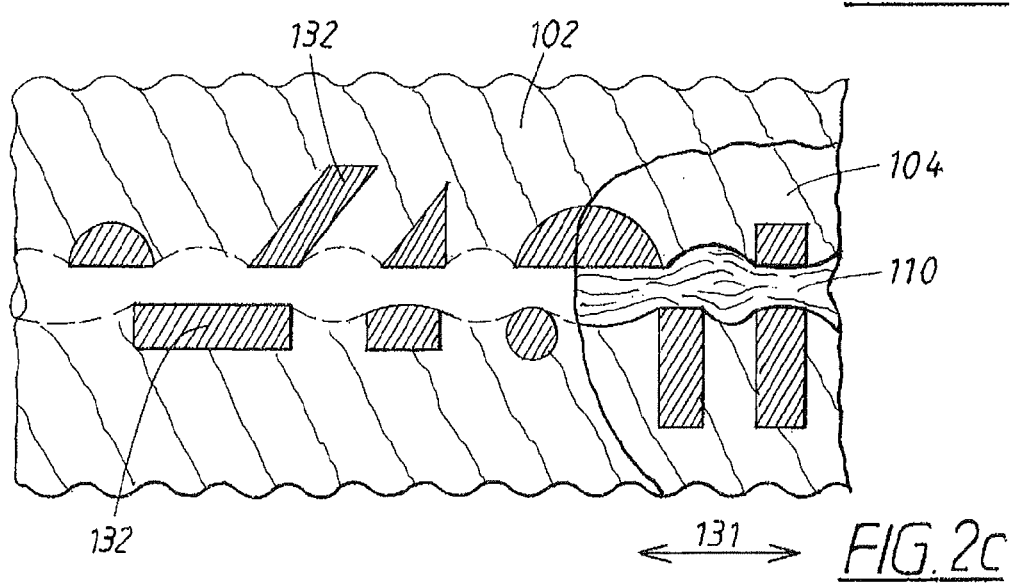
FIG. 2c depicts possible variations for the positioning and form of connecting elements arranged to anchor an elastic element between the liquid-permeable covering layer and the backing layer of a diaper.

FIG. 2c depicts a further example of how an elastic element 110 is anchored between the liquid-permeable covering layer 102 and the backing layer 104. It can be appreciated from FIG. 2c that it is possible to vary both the form and the size and the mutual distance between the different connecting elements 132. As in FIG. 2b, only the anchoring of a single elastic element 110 is depicted, although the same principle applies to the anchoring of all the elastic elements 110 that are present in the elasticated area.

The connecting elements 132 are arranged in rows to either side of the elastic elements 110. The elastic elements 110 are anchored between the fluid-permeable covering layer 102 and the backing layer 104 by the fact that the elastic elements have been extended, whereupon the connecting elements 132 have been applied along the elastic elements 110. When the tension in the elements 110 is subsequently released, the elements contract in their longitudinal direction and extend simultaneously in the direction of their thickness. This means that the constricted space between the liquid-permeable covering layer 102, the backing layer 104 and the connecting elements 132 in the two rows of connecting elements 132 that are arranged to either side of each elastic element 110 are occupied fully by the elastic element 110. As can be appreciated from FIGS. 2a-2c, small protuberances are also formed on the elastic element in the gap between the connecting elements 132 within one and the same row of connecting elements 132. These protuberances consist of elastic material that has been able to expand without being prevented from doing so by the connecting elements 132. A mechanical locking of the elastic elements takes place instead in the areas between the rows of connecting elements 132, where expansion is more restricted.

The diaper 101 is characterized primarily in that the waist elastic 125 of the diaper 101 comprises a patterned area 133 containing a visible pattern 118 in the form of a large letter M.

Figure 3:
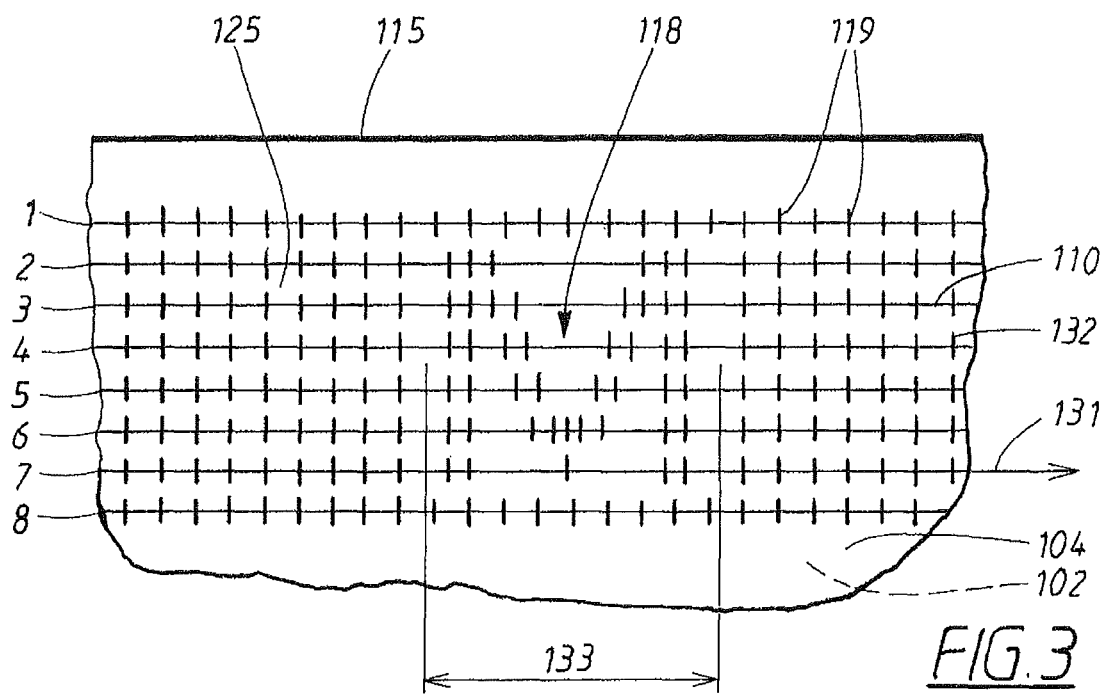
FIG. 3 depicts a part of a waist elastic comprising a pattern in accordance with the invention.

FIG. 3 depicts an enlarged illustration of the area in the waist elastic 125 of the diaper 101 (see FIG. 1b), which comprises the pattern 118 in the form of the letter M. The figure depicts the waist elastic 125 viewed from the side which is intended to face away from the wearer when the diaper is being worn.

The waist elastic 125 consists of eight elastic elements 110, the pattern 118 being arranged on the six middle elements 110. The eight elastic elements 110 are numbered from 1-8 in FIG. 3, the element 110 closest to the rear transverse edge 115 of the diaper 101 having the number 1, and the element 110 furthest away from the edge 115 having the number 8.

The uppermost elastic element 110 (number 1) and the lowermost elastic element 110 (number 8) comprise only the connecting areas 119 that are distributed continuously along the direction of extension 131 of the elements 110.

The other elastic elements 110, that is to say element numbers 2-7, all comprise sections along their direction of extension 131, on which the connecting areas 119 are arranged with varying mutual distances. The lines containing these connecting areas 119 with varying mutual distances together constitute the pattern 118 and are all arranged within the so-called patterned area 133.

The variations in the mutual distances between the connecting areas 119 are different for the different elastic elements 110 (numbers 2-7), the variations in the mutual distances for the respective elements 110 being selected so that the connection areas 119 together constitute a pattern in the form of a letter M. The pattern in this case is formed by the discreet visible connecting elements 132, which in pairs constitute the connecting areas 119 which anchor the respective elastic elements 110 between the backing layer 104 and the liquid-permeable covering layer 102, as illustrated in FIG. 3.

Due to the fact that both the liquid-permeable covering layer 102 and the backing layer 104 consist of comparatively bulky nonwoven materials, the densifications (embossings) of the materials which the connecting elements 132 of the connecting areas 119 form are particularly clearly visible against the background material, as described above.

Embossing usually also means that the densified embossing areas exhibit shinier surfaces compared with the non-embossed background material, which means that the embossed pattern 118 has a more conspicuous appearance.

In alternative embodiments, the backing layer 104 and/or the liquid-permeable covering layer 102 can consist of other types of material. For example, one of the backing layer 104 or the liquid-permeable covering layer 102 can consist of a less bulky material, in which case the densifications (embossings) which constitute the pattern are slightly less conspicuous against the background but still completely visible. The normally modified structure of the embossing surface, that is to say the increased shininess of the embossing surfaces, is particularly important for these less bulky materials in order for the pattern to have a more conspicuous appearance.

It is also conceivable, for other alternative embodiments, to add some form of colour pigment during embossing to ensure that the pattern is more conspicuous against the background material. It is appropriate in this case to coat the unit that produces the embossing surfaces with a colour pigment immediately before the embossing operation is performed. One example of such coating with a colour pigment is described in International Patent Application WO 2004/057 110.

In alternative embodiments, the pattern can consist of an entire line of text, an image or a symbol.

The pattern can relate to an instruction about the handling of the article, the size of the article or the like. Trademarks are other commonly encountered patterns on absorbent articles.

Figure 4:
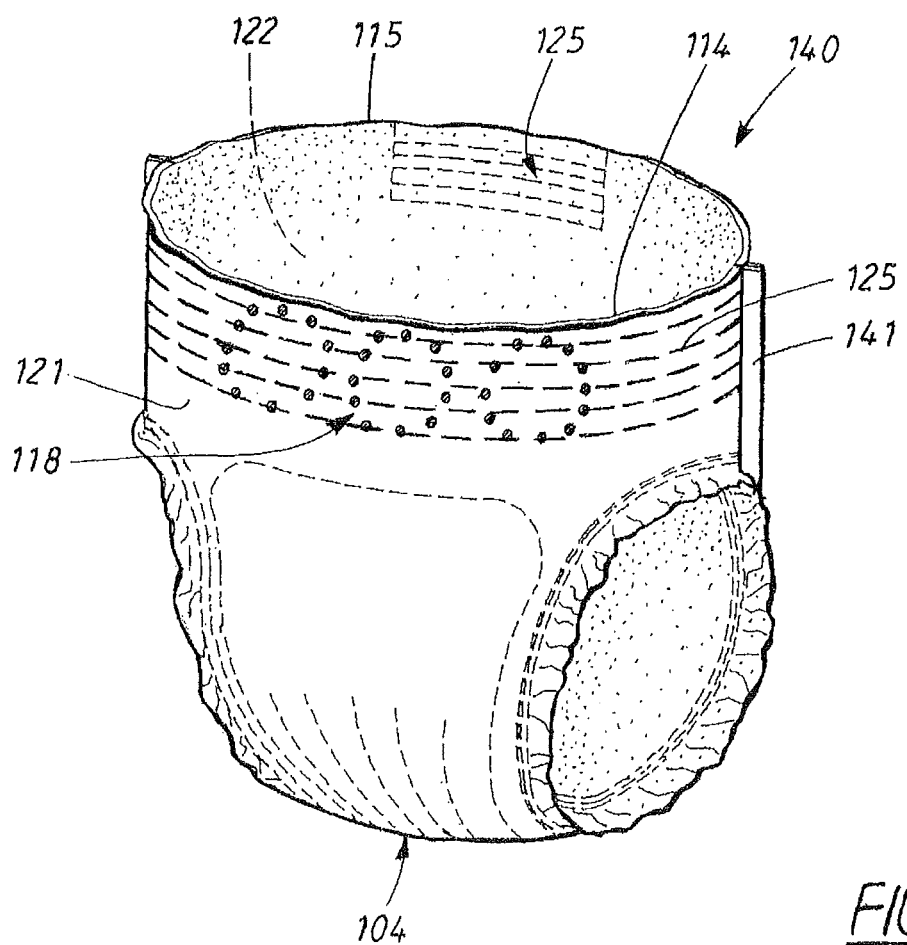
FIG. 4 depicts a pant diaper in a wearer-like configuration comprising a pattern in accordance with the invention.

FIG. 4 depicts a pant diaper 140 intended primarily for incontinent adult wearers.

The pant diaper 140, which is illustrated from the front in a configuration that simulates the wearing of the diaper, is constructed largely in the same way as the open diaper 101 in FIG. 1a and FIG. 1b.

The pant diaper 140 differs primarily from the open diaper 101 depicted in FIG. 1 in that the pant diaper 140 is intended to be put on a wearer in the same way as a pair of underpants, that is to say passed over the legs. The front end section 121 and the rear end section 122 of the pant diaper 140 are already attached to one another in this case on the side sections of the pant diaper 140 during manufacture, as a result of which the pant diaper 140 will have adopted the form of a pant.

The respective side connection 141 consists of an ultrasonic weld, although in alternative embodiments it can consist of a glued joint, a heat-welded joint, a stitched joint or the like.

It is customary today for pant diapers 140 to be capable of being opened and reclosed, in conjunction with which the side connections 141 between the end sections 121, 122 of the pant diaper 140 can be opened to permit inspection of the pant diaper 140 when it is being worn, and subsequently of being reclosed in order to permit its continued use. It is usual for the pant diaper 140 to have been provided with attachment flaps (not illustrated in the figure), which can be used for its reclosure once the prefabricated side connections 141 have been opened and rendered unserviceable.

Openable, or undoable, pant diapers 140 are also advantageous when the pant diaper 140 must be removed from a wearer after use, especially if the pant diaper 140 is smeared with faeces. The side connections 141 of the pant diaper 140 in this case can be opened when the diaper is to be removed from a wearer, with the result that the contaminated pant diaper 140 does not require to be passed over the wearer's legs and feet in conjunction with its removal.

The front end section 121 of the pant diaper 140 exhibits a front waist elastic 125 along its entire extent arranged parallel with and adjacent to the front transverse edge 114. The rear end section 122 exhibits a rear waist elastic 125, which only extends along a part of the extension of the rear end section 122. The rear waist elastic 125 is arranged essentially centrally between the side connections 141 of the pant diaper 140. Both the front and the rear waist elastics 125 are arranged between the liquid-permeable covering layer 102 and the backing layer 104, whereby the waist elastic constitutes an integral part of the two layers 102, 104.

In alternative embodiments, the rear waist elastic 125 can extend over the entire rear end section 122.

Alternatively, the waist elastic 125 can consist of a separate waistband that is attached to the liquid-permeable covering layer 102 and/or the backing layer 104 by means of an appropriate method such as gluing, ultrasonic welding, thermal welding or the like. The waistband in this case is constructed in the same way as the integrated waist elastic, that is to say a flexible strip of material to either side of essentially parallel elastic elements, the elastic elements being anchored to the strips of material as described above. The separate waistband can be prefabricated or manufactured in parallel in the machine used for the manufacture of pant diapers.

The pant diaper 140 exhibits a pattern 118 arranged on the waist elastic 125 in the front end section 121.

The pattern consists of three circles of only cosmetic value without any informative value, such as a trade mark or handling information, for example (which can naturally also constitute a pattern). The pattern 118 is created in the same way as described above (FIG. 3), which means that the respective circle consists of a number of connecting elements 132. The connecting elements 132 exhibit varying mutual distances along the extent of individual elastic elements 110 and between different elastic elements 110 in the area in which the pattern is arranged.

In alternative embodiments, the pant diaper can also comprise patterns 118 on that part of the waist elastic 125 of the pant diaper 140 that is arranged in the rear end section 122.

Pant diapers 140 containing a waist elastic 125 around the whole of their periphery can comprise patterns 118 along the whole of their periphery.

Figure 5:
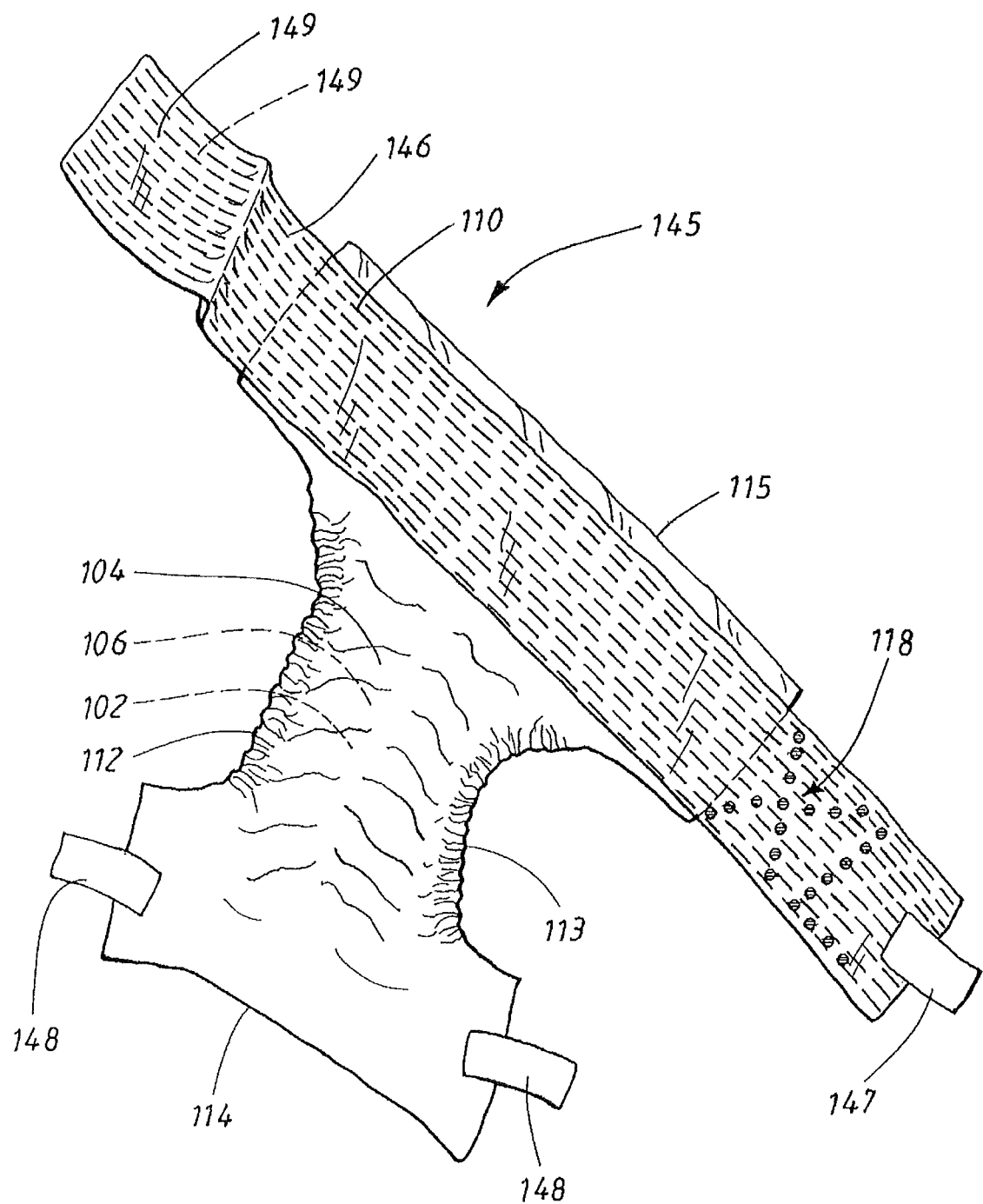
FIG. 5 depicts a so-called belt diaper from the side that is intended to face away from the wearer and which comprises a pattern in accordance with the invention.

FIG. 5 depicts a so-called belt diaper 145 in accordance with the invention from the side that is intended to face away from the wearer when the diaper is being worn.

The belt diaper 145 differs from an open diaper in that its attachment arrangement comprises an elastic belt 146 intended to enfold the wearer's waist, the belt comprising a securing device 147 for securing the belt 146 around the wearer's waist.

The belt 146 is attached to the rear transverse edge 115 of the belt diaper 145 and extends in a transverse direction in relation to the absorption body 106 of the belt diaper 145.

In alternative embodiments, the belt diaper 145 can comprise two belt halves, the respective half of the belt being joined together with the liquid-permeable covering layer 102 and/or the backing layer 104 of the belt diaper 145 on the longitudinal edges 112, 113 of the belt diaper 145 adjacent to the rear transverse edge 115.

The attachment arrangement also comprises two front securing devices 148 arranged on the longitudinal edges 112, 113 of the belt diaper 145 adjacent to the front transverse edge 114. The front securing devices 148 are intended to be secured to the side of the elastic belt 146 facing away from the wearer in conjunction with putting the belt diaper 145 on a wearer.

In alternative embodiments, the front securing devices 148 can comprise adhesive elements intended to be fixed to the surface of the belt 146 oriented away from the wearer. The belt 146 in this case must comprise surfaces intended for interaction with the adhesive elements.

When the belt diaper 145 is to be put on a wearer, the belt 146 is secured around the wearer's waist as a first step. The absorption part of the belt diaper 145 comprising, among other things, the front transverse edge 114 and the absorption body 106, is then passed between the wearer's legs, whereupon two front securing devices 148 are finally attached to the side of the belt 146 oriented away from the wearer.

The belt 146 comprises two flexible nonwoven layers 149 having a number of thread-shaped elastic elements 110 between the nonwoven layers 149. The elastic elements 110 are anchored between the nonwoven layers in the manner illustrated in FIG. 2a above.

In alternative embodiments, the two nonwoven layers 149 can naturally consist of a folded nonwoven strip.

The belt 146 is elastic for its entire length, although in alternative embodiments it can be elastic only in certain sections of its length. It is customary, for example, for the belt 146 to be elastic only in those areas which extend beyond the backing layer 104.

A pattern 118 is arranged on the elastic belt 146.

The pattern 118 consists of the size indication "XL" (extra large) and is arranged on the side of the elastic belt 146 that faces away from the wearer when the belt diaper is put on a wearer. The pattern 118 is created in the same way as described above (FIG. 3), which means that the pattern 118 is constituted by a number of connecting elements, the connecting elements exhibiting varying mutual distances, on the one hand along the extent of individual elastic elements 110, and on the other hand between the different elastic elements 110 that are present in the area in which the pattern is arranged.

The invention also comprises all conceivable combinations of the described illustrative embodiments.

The invention is also not restricted to the above-mentioned illustrative embodiments, but is, of course, also applicable to other embodiments within the scope of the following patent claims.

The invention claimed is:

1. An absorbent article comprising at least one elasticated area, the elasticated area comprising a first layer and a second layer of material together with a plurality of thread-shaped elastic elements oriented essentially in parallel and arranged between the first and second layers of material, the elasticated area comprising discreet connecting elements arranged in rows to either side of each of the elastic elements, the connecting elements connecting the first and second layers of material in such a way that, together with the first and second layers of material, they form constricted passages, through which the elastic elements run, the elastic elements being mechanically anchored in the constricted passages, wherein the elasticated area comprises a patterned area, the connecting elements are arranged in rows along a respective elastic element of the elastic elements which run through the patterned area, and in the patterned area at least some of the connecting elements in the same row are arranged at varying distances relative to one another or exhibit a varying extent parallel to the elastic elements so that the distances or extent of the connecting elements in the patterned area are different than that of the connecting elements outside of the patterned area, such that the connecting elements in the patterned area form a visible pattern that distinguishes the patterned area from the remainder of the elasticated area, the visible pattern being in a form of a text, image or symbol.

2. The absorbent article according to claim 1, wherein the connecting elements are arranged in pairs to either side of the elastic elements, each pair of connecting elements forming a connecting area, the connecting areas forming the visible pattern.

3. The absorbent article according to claim 2, wherein the connecting elements in each pair have the same form and size.

4. The absorbent article according to claim 1, wherein the pattern is arranged on a waist elastic of the absorbent article.

5. The absorbent article according to claim 4, wherein the waist elastic comprising the pattern consists of a separate waistband.

6. The absorbent article according to claim 4, wherein the pattern is arranged on the waist elastic arranged in a rear end section of the article.

7. The absorbent article according to claim 4, wherein the pattern is arranged on the waist elastic arranged in a front end section of the article.

8. The absorbent article according to claim 1, wherein the article is a pant diaper.

9. The absorbent article according to claim 1, wherein the article is a belt diaper.

10. The absorbent article according to claim 1, wherein the pattern constitutes a size indication.

11. The absorbent article according to claim 1, wherein the pattern constitutes a handling instruction.

12. The absorbent article according to claim 1, wherein the pattern indicates which is a front or rear of the absorbent article.

13. The absorbent article according to claim 2, wherein the pattern is arranged on a waist elastic of the absorbent article.

14. The absorbent article according to claim 3, wherein the pattern is arranged on a waist elastic of the absorbent article.

15. The absorbent article according to claim 5, wherein the pattern is arranged on the waist elastic arranged in a rear end section of the article.

16. The absorbent article according to claim 5, wherein the pattern is arranged on the waist elastic arranged in a front end section of the article.

\* \* \* \* \*